United States Patent [19]

Di Schiena et al.

[11] Patent Number: 4,840,964
[45] Date of Patent: Jun. 20, 1989

[54] TAURINE DERIVATIVE, ITS PREPARATION AND PHARMACEUTICAL COMPOSITIONS CONTAINING IT

[75] Inventors: Michele G. Di Schiena; Vittoria Orru, both of Cisliano, Italy

[73] Assignee: Ricerche di Schiena S.n.c. del Dr. Michele G. di Schiena & C., Milan, Italy

[21] Appl. No.: 234,181

[22] Filed: Aug. 22, 1988

[30] Foreign Application Priority Data

Sep. 18, 1987 [IT] Italy ................................. 21958 A/87

[51] Int. Cl.$^4$ ..................... A61K 31/38; C07D 333/02
[52] U.S. Cl. ........................................ 514/448; 549/72
[58] Field of Search ........................... 549/72; 514/448

[56] References Cited

U.S. PATENT DOCUMENTS 4,210,666 7/1980 Munson ................................. 549/72

Primary Examiner—Alan Siegel
Attorney, Agent, or Firm—Walter H. Schneider

[57] ABSTRACT

The taurinamide with 2-thenoic acid of formula

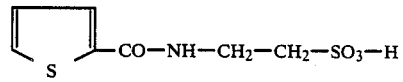

prepared by reaction of taurine with an acylating derivative of 2-thenoic acid, is useful in human and veterinary medicine.

2 Claims, No Drawings

TAURINE DERIVATIVE, ITS PREPARATION AND PHARMACEUTICAL COMPOSITIONS CONTAINING IT

The present invention refers to the compound of formula

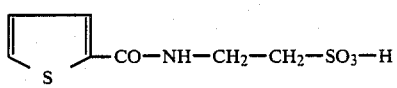

to a process for the preparation thereof and to pharmaceutical or veterinary composition containing it as an active principle.

The compound of formula I is the amide of taurine with 2-thenoic acid.

The invention refers also to salts of compound I with pharmaceutically acceptable organic or inorganic bases.

Taurine, or 2-aminoethanesulfonic acid, is a physiological compound endowed with several actions, namely it regulates metabolism by activating tissue nutrition, favouring the oxygen exchange between blood and tissues and regulating the transmembrane equilibria of the potassium and calcium ions; it is also known the role of taurine in the conjugation of biliary acids and as a neurotrasmitter.

It has been already proposed the therapeutic use of taurine, for instance for the treatment of pathologies of the cardio-vascular, broncho-pulmonary, neuromuscular system or as detoxicant and radio-protecting drug.

It has now been found that the compound of the invention enhances the therapeutic properties of taurine, widening its applicative possibilities and improving the pharmacokinetics properties, particularly absorption.

The compound of the invention proved to be particularly useful as mucolytic, hepato-protective, detoxicant, normolipemizing, antiischemic, radioprotective agent and in the treatment of some epileptic forms.

Examples of pathological conditions which may be effectively treated with compound I comprise: broncho-pulmonary affections with staunching of secretions, qualitative and quantitative changes of alveolar surfactant, peripheral arteriopathies, angina pectoris, acute and chronic coronary cardiopathies, acute and chronic cerebral vasculopathies, exogeneous and endogenous toxic conditions and hepatopathies related therewith, conditions of impaired lipidic equilibrium.

As above reported, the compound of the invention may also be useful for treating some epileptic forms and in the prophylaxis and protection from exposure to ionizing radiations (UV, X or gamma rays).

Experiments carried out on animals and patients in comparison with taurine and, in the case of tests on the ability of the compound under exam to change the rheologic properties of the expectorate, with acetylcysteine and carbocysteine, have shown an higher, statistically significant efficacy of the compound of the invention with respect to the reference standards.

The compound is also practically non-toxic since doses as high as 4000 mg/kg in mice and rats, both orally and i.p., did not cause either toxic effects or deaths.

For the considered therapeutic uses, the compound I may be administered by the oral, parenteral, rectal or topic in form of suitable pharmaceutical compositions, prepared according to usual techniques and excipients, such as those described in Remington's Pharmaceutical Sciences Handbook, Hack Pub. Co., N.Y. U.S.A.

The topical route may be usefully used for pharmaceutical compositions having mucolytic activity: suited forms are, in this case, aereosol, atomized powders, solutions for nasal, bronchial or endoauricular installations.

Examples of other suited pharmaceutical forms, both for the use as mucolytic and as a drug active in the other pathological conditions, comprise tablets, capsules, granulates, syrups, suspensions, drops, "release" or gastro-resistant forms, suppositories or rectioles for the rectal routes and liquid or lyophilized vials for the parenteral route.

The compositios of the invention may also contain other active principles having complementary, synergic or anyhow useful activity.

For instance, in the compositions to be used as mucolytics, the combination with antibiotics (chloramphenicol), balsamics (guaiacol, timol, menthol), expectorants (terpine), cough sedatives (codeine), broncho-dilators (theophylline), enzymes (chymotrypsine, bromelain, papaine), antidyspnoics (sobrerol), anti-asmathics (sodium chromoglycate), anti-inflammatories (steroids and FANS), antihistaminics (1-chlorphenamine), antivirals (amantadine) and the like, may be useful. For the other applications, useful combinations may be, inter alia, those with cholic acids (e.g. desoxycholic, ursodeoxycholic, chenodesoxycholic acids), glycerophosphates, liver extracts, vitamins, tonics of the muscular and nervous system, antilipemics, hepatoprotecting or mucolytic agents.

The posology of compound I will depend or several factors such as the therapeutic indication, patent's weight and conditions etc.

For instance, as a mucolytic, the average dosage may range from 50 mg to 1000 mg for unit dose, once or more times a day.

In the other cases, the posology may range from 0.1 to 3 g per dose.

Higher dosages may also be used in view of the veng low toxicity of the compound I.

The compound of the invention may be prepared by per se known methods and substantially comprising the reaction of an acylating derivative of 2-thenoic acid with taurine.

For instance, the chloride of 2-thenoic acid may be used and, in this case, the reaction is preferably carried out in the presence of an acidity acceptor such as sodium bicarbonate, triethylamine, pyridine. As a reaction medium, it is possible to use all those solvents which are inert in the reaction conditions, such as acetone. The hydration degree may range within wide limits, from 0 to 99%. The temperature is not critical but it is preferably ranging from 0° to +30° C.

The following examples further illustrate the invention, without limiting it in any way.

EXAMPLE 1

6 g of 97% 2-thenoic acid chloride dispersed in 50 30 ml of acetone were adeed dropwise to a mixture of 5 g of taurine, 10 g of sodium bicarbonate, 100 ml of water and 150 ml of acetone, vigorously stirred and cooled to 0° C. When the addition was complete, the temperature was allowed to raise to about 20° C., leaving the mixture at this temperature for some hours.

The residual solid was filtered washing with 20 ml of 50% aqueous acetone.

The filtered solution was evaporated under reduced pressure at 50° external.

The residual aqueous solution was percolated on a Amberlite IR 120$^R$ H+ resin column (0 30 mm; H 300 mm).

The acidic effluent, together with the washings, was evaporated to dryness, under reduced pressure, at max 40° external.

The residue was washed with ethyl ether (20 ml×3) and then evaporated under vacuum.

5g of the compound of formula I were obtained.
Analytical data
M.W. 235,3
Aspect: crystalline solid
Solubility: very soluble in water, practically insoluble in ether;
TLC (Silicagel F254, eluent: ethyl acetate/acetone/$CH_3CO_2H/H_2O$
(50:20:10:10) Rf 0,45 (Rf taurine 0,10;
R.f. 2-thenoic acid=0,05).
NMR ($D_2O$) : 3.2 (2H, t); 3.76 (2H, t); 7.16 (1H, t); 7.66 (2H, t).
IR(KBr) cm$^{-1}$: 3350, 1620, 1540, 1400, 1200.

EXAMPLE 2

0.400 g of NaOH were carefully added to 2.35 g of the compound of Example 1, dissolved in 50 ml of water.

The solution was evaporated to dryness under reduced pressure and at max 40° external.

The sodium salt of I was obtained in quantitative yield. By the same method, substituting the sodium hydroxide with the suited base, the salts of potassium, lithium, calcium, magnesium, selenium, iron, copper, zinc, gold, silver, platinum, manganese, cobalt, triethylamine, diethylamine, urotropine, trishydroxymethylaminomethane, choline, arginine, methionine, cysteine, citrulline, histidine, S-adenosyl methionine, amantadine, hydroxyethylpyrrolidine, morpholine, imidazole, carnitine inner salt, meglumine, glycine, betaine, lysine, colestyramine, diethanolamine, were obtained.

EXAMPLE 3

2.5 g of Taurine and 1.7 g of $NaHCO_3$ were dissolved in 25 ml of water.

After addition dropwise of 75 ml of acetone, 3.3 g of AgO were added at 0° C., to the suspension protected from direct light.

3.1 g of 2-thenoyl chloride dispersed in 10 ml of acetone were added thereto and the reaction was left at room temperature for some hours, up to disappearance of Taurine (TLC). The mixture was then filtered on celite, and the filtrate, which must be free from chlorides, evaporated to small volume. The residue was treated with 100 ml of acetone under stirring till complete transformation in crystalline solid which was pump-filtered, washed with acetone and dried at 50°max. yield: 4 g. m.p. 284°-288° C. Analytical properties identical to those of Example 1.

We claim:

1. A compound of the formula

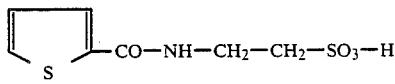

and its salts with pharmaceutically acceptable organic or inorganic bases.

2. A pharmaceutical composition containing as the principal active ingredient a compound according to claim 1 in admixture with a pharmaceutically acceptable carrier therefor.

* * * * *